United States Patent [19]
Piotrowski et al.

[11] Patent Number: 5,277,878
[45] Date of Patent: Jan. 11, 1994

[54] REACTOR FOR HETEROGENEOUS-PHASE REACTIONS

[75] Inventors: Bernhard Piotrowski, Lohmar; Hermann-Josef Korte, Haltern, both of Fed. Rep. of Germany

[73] Assignee: Huels Aktiengesellschaft, Marl, Fed. Rep. of Germany

[21] Appl. No.: 889,339

[22] Filed: May 28, 1992

[30] Foreign Application Priority Data

May 29, 1991 [DE] Fed. Rep. of Germany ....... 4117592

[51] Int. Cl.⁵ .............................................. B01J 10/00
[52] U.S. Cl. .................................. 422/129; 422/198; 422/200; 422/224; 422/231; 422/234; 261/153; 261/36.1; 261/121.1; 261/124
[58] Field of Search ............... 422/198, 202, 201, 231, 422/234, 285, 288, 290, 224, 129; 261/153, 36.1, 121.1, 124; 34/22; 55/93, 94, 90, 89; 210/456, 188, 180; 435/316, 313, 314

[56] References Cited

U.S. PATENT DOCUMENTS

| | | | |
|---|---|---|---|
| 924,592 | 6/1909 | Steynis | 261/124 |
| 2,869,844 | 1/1959 | Thomas | 261/124 |
| 3,406,220 | 10/1968 | Hawkins | 261/36.1 |
| 3,759,669 | 9/1973 | Aaron et al. | 422/231 |
| 3,846,079 | 11/1974 | Alagy et al. | 261/36.1 |
| 3,927,987 | 12/1975 | Winter, III et al. | 422/200 |
| 4,146,578 | 3/1979 | Brennan et al. | 423/473 |
| 4,275,032 | 6/1981 | Anderson | 422/224 |
| 4,342,876 | 8/1982 | Klingman | 422/231 |
| 4,545,945 | 10/1985 | Präve et al. | 422/231 |
| 4,672,142 | 6/1987 | Hundeck et al. | 570/247 |
| 4,844,876 | 7/1989 | Oliveau et al. | 55/93 |

FOREIGN PATENT DOCUMENTS 0075742  9/1982  European Pat. Off. .

Primary Examiner—Robert J. Warden
Assistant Examiner—Hien Tran
Attorney, Agent, or Firm—Millen, White, Zelano & Branigan

[57] ABSTRACT

A reactor for carrying out heterogeneous-phase reactions, in particular gas/liquid reactions with a continuous liquid phase and a dispersed (discontinuous) gas phase, is described, in which, in a horizontal plane, a substantially vertically upward-directed flow of the reaction medium takes place in a first region of the reactor cross-section and a substantially vertically downward-directed flow takes place in another region of the reactor having a device for dispersing the discontinuous phase such as a dispersing screen, substantially only in the regions with upward-directed flow. The reactor is here designed in such a way that free flow of the reaction medium from regions with downward-directed flow to regions with upward-directed flow is possible in the region of the dispersing device. The preferred use of the proposed reactor is the exothermic oxidation of p-xylene and monomethyl p-toluate with air in the so-called Witten DMT process.

11 Claims, 1 Drawing Sheet

REACTOR FOR HETEROGENEOUS-PHASE REACTIONS

SUMMARY OF THE INVENTION

The invention relates to a reactor for Carrying out heterogeneous-phase reactions, in which, in a horizontal plane, a substantially vertically upward-directed flow of reaction medium occurs in at least one region of the reactor cross-section and a substantially vertically downward-directed flow occurs in at least one other region, the reactor having means for dispersing the discontinuous (disperse) phase substantially only in the region(s) with upward-directed flow.

In heterogeneous-phase reactions, in particular gas/liquid reactions with a continuous liquid phase and a dispersed gas phase, the mass transfer and/or heat transfer processes, necessary for the reaction, through the phase boundary are frequently decisive for the course of the reaction and for the yield from the reactor. Above all for exothermic reactions with a continuous liquid phase and a dispersed gaseous phase, a conglomeration of the gas bubbles must be avoided.

The present invention relates especially to a reactor for carrying out the highly exothermic oxidation reaction of p-xylene and monomethyl p-toluate with air in the so-called Witten DMT process (DE-C3-2,805,915, DE-C2-3,704,720 WO-90/09,367). It is a characteristic of this reaction that a high proportion of inert gas must be passed with the oxygen through the reactor, whereby an undesired bubble conglomeration is promoted.

Diverse basic types of reactors for heterogeneous-phase reactions are known from Ullman, Encyclopedia, Volume 3, pages 357 et seq. (1973).

The oxidation of p-xylene and monomethyl p-toluate with air is, in existing plants, predominantly carried out in simple bubble column reactors without dispersing devices, in which the oxygen-containing reaction gas is introduced centrally in the lower part of the reactor. After a short flow distance, a major part of the bubbles coalesce to form large bubble agglomerates, which determine the liquid circulation. In these reactors, the heat exchangers are arranged horizontally in an outer annular space in the vicinity of the vessel wall. The liquid reaction medium flows downwards again along these heat exchanger tubes and is entrained upwards anew by the bubbles (principle of the air-lift pump).

The appearance of large bubbles in the reactors causes the following undesired phenomena:
- high foam formation at the top of the reactor,
- yield loss caused by the heat of reaction not being removed in the interspaces between the gas bubbles,
- high circulation rates of the liquid with short-circuit streams caused in part thereby.

These disadvantages manifest themselves, on the one hand, in the achievable oxidation yield and in the sometimes unstable behavior of the reactors caused by fluid dynamics.

U.S. Pat. No. 4,342,876 has disclosed a loop reactor for carrying out the oxidation reaction of p-xylene and monomethyl p-toluate with air, in which the liquid reactants and the oxygen-containing air are mixed in a first reactor section with the circulating reaction medium, and reacted. In a reactor section separate therefrom, the reaction medium heated up by the reaction and with the liquid products contained therein is cooled by flowing along heat exchanger tubes. The circulation of the reaction medium is maintained by the difference in the densities of the two phases.

In this reactor, there is a risk of the gaseous phase, introduced in the form of bubbles into the reactor, conglomerating to form large bubbles, whereby the phase boundary area and hence the reaction rate is reduced, on the one hand, and the liquid phase enclosed between the large gas bubbles is insufficiently mixed, on the other hand, whereby high temperature peaks and hence yield losses can be caused.

EP-A1-0,075,742 has disclosed a loop reactor of the generic type for carrying out a gas/liquid reaction, in which the gaseous phase and the liquid phase are introduced at the bottom of the reactor into an open internal cylinder as a mixing zone. The mixing zone is provided with packing or internals, not described in more detail. Redispersing of the gas bubbles is achieved in this way. In this type of reactor, the heat of reaction is removed by vaporization of liquid reaction medium. A reactor of this type cannot be used for the oxidation reaction of p-xylene and monomethyl p-toluate with air due to the occurrence of a strongly exothermic reaction occurring in the lower region of the packing causing production of byproducts and reduction of yield.

Therefore, an object of the present invention is to provide a reactor of the generic bubble column type, which can be used for carrying out the oxidation reaction of p-xylene and monomethyl p-toluate with air and in which the appearance of temperature peaks is avoided.

Another object of the invention is to increase the yield of the reactor. A further object of the invention is to improve the removal of heat in exothermic reactions, to reduce the appearance of large bubbles and to ensure a more homogeneous temperature distribution within the reactor.

Furthermore, it is also intended that the invention should allow an inexpensive modification of existing reactors.

Upon further study of the specification and appended claims, further objects and advantages of this invention will become apparent to those skilled in the art.

These objects are achieved by a reactor of the generic type described above but wherein free flow of reaction medium is provided from the region(s) with a downward-directed flow to region(s) with upward-directed flow in the region of dispersing means.

Thus, the objects of the invention can be obtained by a reactor for carrying out heterogeneous-phase reactions between a continuous, heavier, liquid phase and a discontinuous, lighter gas phase, wherein, in a horizontal plane, a substantially vertically upward-directed flow of reaction medium occurs in at least one region of the reaction cross-section and a substantially vertically downward-directed flow of reaction medium occurs in at least one other region, the reactor having means for dispersing the discontinuous phase substantially only in the region(s) with upward-directed flow, the improvement comprising providing for free flow of reaction medium from region(s) with downward-directed flow to region(s) with upward-directed flow in the region of the dispersing means.

In contrast to conventional loop reactors, the inner region of the reactor with an upward-directed flow is in this case not separated from the outer annular reactor space. In spite of the dispersing screens preferably used as (re)dispersing devices and having a small passage cross-section of preferably <30% of the cross-sectional area, the bubbles are not deflected into the outer reactor cross-section. Rather, all the bubbles pass through the screens, thus renewing their (phase) surface area.

Preferably, the reactor contains 1-10 dispersing screens. The diameter of the perforations in the screens are preferably about 1-25 mm.

The main flow in the reactor is upward-directed in the reactor interior, the region of the dispersing devices, due to the lower density of the bubbles. From the inner reactor space, the main flow is deflected outwards at the top in the region of the liquid level and passes down again on the outside along the vessel wall (annular space). It is here that the cooling of the reaction medium preferably takes place, for example by means of flow along the outside of cooling tubes, i.e., by indirect heat exchange. In addition to this main flow, there is also crossflow, provided according to the invention, from the outer annular reactor space to the inner reactor space with upward-directed flow, that is to say to the dispersing devices, which effects a cooling of the reaction medium at this point and additional mixing of the liquid phase.

A particular advantage of the invention is that even existing bubble column reactors, such as are usually employed for the reaction of p-xylene and monomethyl p-toluate with air in the Witten DMT process, can be modified inexpensively in accordance with the invention, for example, by installing dispersing screens within the reactor.

In the case where, according to a preferred embodiment of the invention, dispersing screens are used as the means for dispersing the lighter phase (gas phase), the mean mutual spacing of the dispersing screens is preferably 0.5-1.5 times their diameter, the diameter of noncircular screens being taken as the diameter of a circular screen of the same area. The ratio of the diameter of the screens to the diameter of the reactor is preferably about 0.1-0.8.

In principle, heat exchangers can be arranged in the reactor both in the inner region with upward-directed flow and in the outer region with downward-directed flow. In general, however, the heat exchangers are, for constructional reasons, arranged in the outer region, that is to say those regions of the reaction with downward-directed flow.

It is particularly advantageous if the disperse (discontinuous) lighter phase is introduced into the reactor in the region of the dispersing screens. For this purpose, a fairly large number of air nozzles arranged vertically on top of one another in different planes are fed from a feed pipe arranged vertically in the reactor. This feeding of the disperse phase in different planes of the reactor in the region of the dispersing screens has particular advantages.

The proportion of the not yet fully reacted reactants in the disperse phase (for example oxygen) can be adjusted to be approximately constant in the vertical direction. Moreover, the freshly introduced gas bubbles assist a cross-mixing of the continuous (liquid) phase and thus ensure an even better temperature equalization. In particular, the synergistic interaction between the possibility of free flow from those regions of the reactor with substantially downward-directed flow and those regions with substantially upward-directed flow to the preferred introduction of the disperse (discontinuous) phase into the reactor in the region of the dispersing screens leads to a considerable increase in the yield from the reactor.

According to a further advantageous embodiment of the invention, the main flow in the reactor—upward-directed in the inner region and downward-directed in the outer region—is additionally assisted, for example by means of a pump. Due to the imparting of a substantially vertically upward-directed central flow of the continuous phase, the conversion and the yield from the reactor are further increased.

Preferably, the wholly or partially reacted lighter phase is taken off at the top, and the heavier phase is taken off at the bottom of the reactor.

BRIEF DESCRIPTION OF THE DRAWINGS

Various other objects, features and attendant advantages of the present invention will be more fully appreciated as the same becomes better understood when considered in conjunction with the accompanying drawing, in which like reference characters designate the same or similar parts throughout the several views, and wherein.

DETAILED DESCRIPTION OF THE DRAWING

Figure 1:
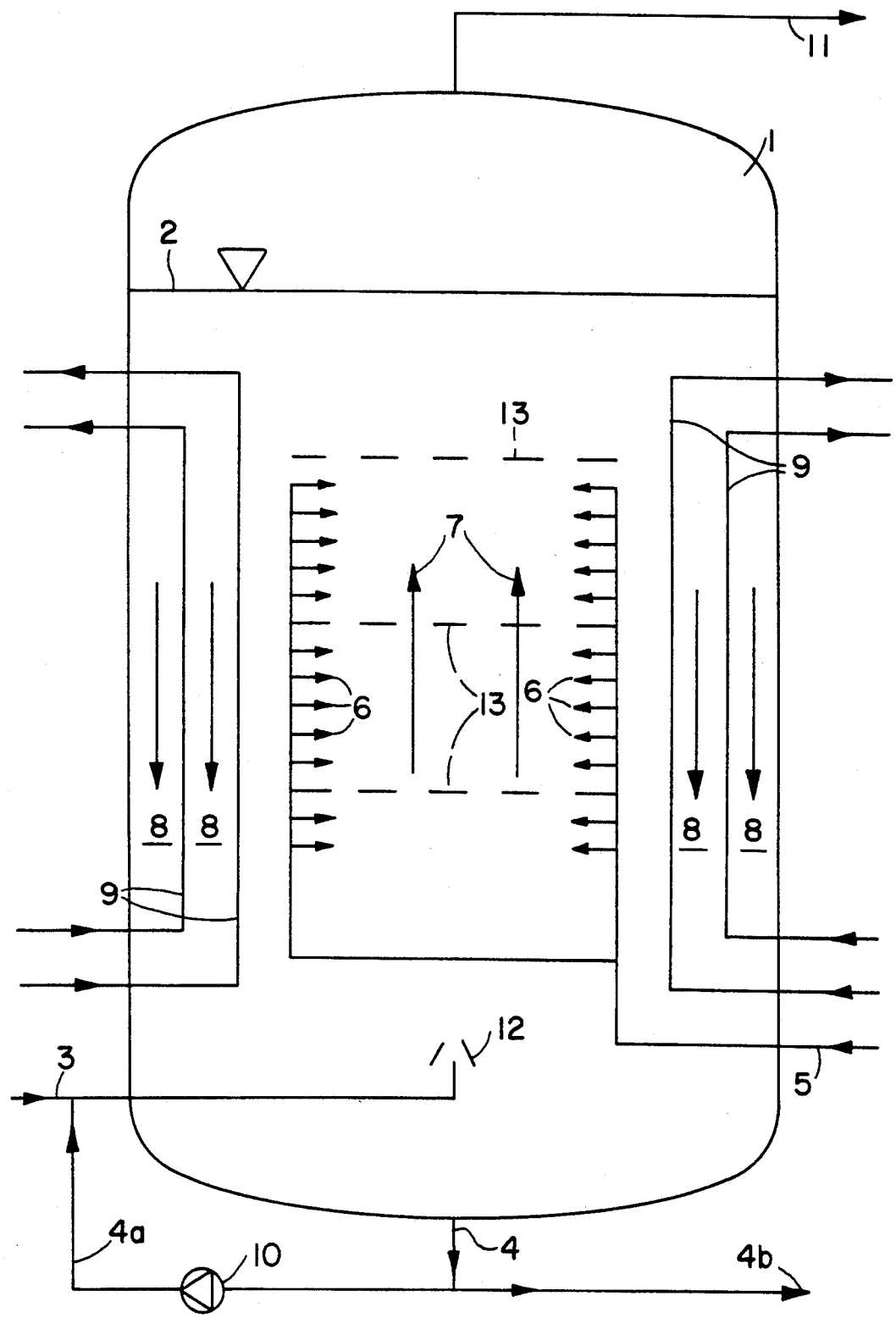
FIG. 1 shows a reactor according to the invention (diagrammatic).

The reactor 1 (e.g., substantially cylindrical) shown in FIG. 1 serves for the oxidation of a mixture of para-xylene (p-X) and methyl para-toluate (p-TE) in the liquid phase in the absence of solvents and halogen compounds at a pressure of about 7 bar and a temperature of about 160° C. with atmospheric oxygen in the presence of dissolved heavy metal oxidation catalysts, for example, in the presence of a mixture of compounds of cobalt and manganese (compare German Patent Specification 2,010,137). A mixture of monomethyl terephthalate (MMT) and p-toluic acid (p-TA) is thus formed. This process has been described in great detail, for example, in DE-A1 39 04 586 (WO 90/09 367).

The heavy oxidate phase 4 is removed at the bottom of the reactor 1. The already very nearly fully reacted heavy oxidate phase is in part recycled by the pump 10 as a circulation stream 4a into the lower part of the reactor 1. The remaining part stream 4b can, however, be fed to a further reaction stage, for example an oxidation stage or esterification stage.

The feed materials 3 such as, for example, p-xylene, monomethyl p-toluate and catalyst, required for the oxidation are mixed into the circulation stream 4a. In order to avoid an undesired discharge of the feed materials 3 with the fully reacted oxidate phase 4 as a result of a short-circuit flow, the feed materials 3 and the circulation stream 4a are introduced into the lower part of the reactor 1 in such a way that a substantially vertically upward-directed flow 7 is imparted. To intensify this flow 7, the feed materials 3 and the circulation stream 4a are introduced into a device, for example a liquid ejector 12, in such a way that a multiple of the feed stream 3 fed and of the circulation stream 4a is utilized for imparting the flow 7. Across this flow 7, the air is passed as a discontinuous lighter phase via the air feed point 5 by means of air nozzles 6 into the region of the dispersing screens 13. The discontinuous lighter phase is thus carried along by the flow 7 and divided up many times and/or dispersed when flowing through the dispersing screens 13. The repeated reformation of the phase boundaries, thus occurring, between the discontinuous and continuous phases leads to a particularly intensive and uniform mass transfer and heat transfer between the two phases.

This process is repeated in an advantageous manner, as shown in FIG. 1, on each dispersing screen 13 until the discontinuous lighter phase, with the oxygen almost completely reacted, leaves the phase boundary 2 of the reaction medium at the top of the reactor as the lighter phase 11. After the vertically upward-directed flow 7 has left the last dispersing screen 13, it is deflected downwards in the region of the phase boundary 2 into the outer region of the reactor and thus forms the downward-directed flow 8. The flow 8 is then taken along the tubes 9 of the heat exchanger arranged in this region, the cooling of the reaction medium taking place preferentially in the flow 8. Portions of this flow 8 are entrained by the air (discontinuous, lighter phase) and thus flow from the outer annular reactor space into the core zone of the reactor, so that additional mixing of the lighter phase with the cooled reaction medium from the flow 8 takes place.

The entire disclosures of all applications, patents and publications, cited above and below, and of corresponding application Federal Republic of Germany P 41 17 592.1, filed May 29, 1991, published on Dec. 3, 1992 as DE 4117592 are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A reactor for performing a heterogenous-phase reaction between at least one liquid reactant and at least one gaseous reactant comprising:
   a reactor of substantially cylindrical shape having an axis, a sidewall, an upper portion and a lower portion;
   liquid inlet means for introducing at least one liquid reactant;
   means for introducing at least one gaseous reactant, positioned above said liquid inlet means;
   means for dispersing gaseous reactant positioned above said liquid inlet means;
   heat exchange means positioned within said reactor adjacent to said sidewall;
   liquid outlet means positioned in said lower portion; and
   gas outlet means positioned in said upper portion,
   wherein said liquid inlet means and said reactor of cylindrical shape generate a first region of substantially upward-directed fluid flow along said axis and in fluid communication therewith along the length of said first region, a second region of substantially downward-directed fluid flow adjacent to said sidewall.

2. A reactor according to claim 1, wherein said means for dispersing gaseous reactant are a plurality of dispersing screens having an open area of less than 30% and having a mean spacing between said dispersing screens of 0.5–1.5 times their diameter.

3. A reactor according to claim 1, wherein said heat exchange means are indirect heat exchangers.

4. A reactor according to claim 1, further comprising recycle means for recycling at least a portion of liquid discharged via said liquid outlet means back to said lower portion of said reactor.

5. A reactor according to claim 2, wherein said heat exchange means are indirect heat exchangers.

6. A reactor according to claim 2, wherein said means for introducing at least one gaseous reactant is positioned in the region of said dispersing screens.

7. A reactor according to claim 6, wherein said means for introducing at least one gaseous reactant is a plurality of vertically arranged nozzles positioned in different horizontal planes above said liquid inlet means.

8. A reactor according to claim 4, wherein said recycle means is connected to said liquid inlet means whereby liquid reactant and said recycled portion of liquid are combined and introduced together and into said reactor.

9. In a method comprising oxidizing p-xylene and monomethyl p-toluate with air in a reactor, the improvement comprising:
   said reactor having a cross-section, a top portion, and a bottom portion,
   generating a substantially vertically upward-directed flow of reaction medium, containing a continuous, heavier, liquid phase and a discontinuous, lighter, gas phase, in at least one region of said reactor and a substantially vertically downward-directed flow of said reaction medium occurs in at least one other adjacent region of said reactor,
   said reactor having means for dispersing said discontinuous, lighter, gas phase substantially only in said at least one region with upward-directed flow, and
   said substantially vertically upward-directed flow of reaction medium and said substantially vertically downward-directed flow of reaction medium being in fluid communication along the length of a vertical boundary between said regions.

10. A method of performing a heterogeneous phase reaction in a reactor between a continuous, heavier, liquid phase and a discontinuous, lighter, gas phase, said method comprising:
   (a) providing a reactor having a sidewall, a longitudinal axis, an upper portion, and a lower portion, said reactor having liquid product removal means located in said lower portion, discharge gas outlet means located in aid upper portion, means for introducing a liquid reactant positioned in said lower portion, means for introducing a gaseous reactant above said means for introducing a liquid reactant, and dispersing means located in a region of said reactor along said longitudinal axis above said means for introducing a liquid reactant;
   (b) introducing said liquid reactant into said region of said reactor along said longitudinal axis to provide an upward directed flow of continuous, heavier, liquid phase therein and to provide a downward-directed flow of continuous, heavier, liquid phase in a region adjacent to said sidewall, wherein said region of upward-directed flow and the region of downward-directed flow are in fluid communication along the lengths thereof; and
   (c) introducing said gaseous reactant into said region of said reactor along said longitudinal axis to generate a discontinuous, lighter, gas phase within said upward-directed flow of continuous, heavier, liquid phase.

11. In a method comprising oxidizing p-xylene and monomethyl p-toluate with air in a reactor, the improvement comprising:
   said reactor having
   a longitudinal axis, a bottom portion,
an upper portion,
a sidewall,
a first outlet means located in said bottom portion of said reactor,
a second outlet means positioned in said upper portion of said reactor,
fluid inlet means in said bottom portion of said reactor and positioned therein to provide a region of upward directed flow within said reactor, said region of upward directed flow having a length along said longitudinal axis, means for introducing a gaseous reactant positioned above said fluid inlet means,
dispersing means located above said fluid inlet means, and
heat exchange means positioned adjacent to said sidewall; and
introducing p-xylene and monomethyl p-toluate into said reactor via said fluid inlet means to generate said region of upward-directed flow and to generate a region of downward directed flow surrounding said region of upward directed flow, wherein said region of upward directed flow and said region of downward directed flow being in fluid communication along the respective lengths.

* * * * *